United States Patent [19]

Moncada et al.

[11] Patent Number: 4,927,417
[45] Date of Patent: May 22, 1990

[54] SAFETY SLEEVE ADAPTER

[75] Inventors: Elizabeth Moncada; Michael B. Schneider, both of Chicago, Ill.

[73] Assignee: Schneider Medical Technologies, Inc., Chicago, Ill.

[21] Appl. No.: 216,001

[22] Filed: Jul. 7, 1988

[51] Int. Cl.$^5$ ............................................. A61M 5/00
[52] U.S. Cl. ...................................... 604/198; 604/263
[58] Field of Search ................. 604/198, 263, 192, 187

[56] References Cited

U.S. PATENT DOCUMENTS

| | | | |
|---|---|---|---|
| 4,425,120 | 1/1984 | Sampson et al. | 604/198 |
| 4,631,057 | 12/1986 | Mitchell | 604/198 |
| 4,654,034 | 3/1987 | Masters et al. | 604/192 |
| 4,664,653 | 5/1987 | Sagstetter et al. | 604/197 |
| 4,664,654 | 4/1987 | Strauss | 604/198 |
| 4,666,435 | 5/1987 | Braginetz | 604/198 |
| 4,668,223 | 5/1987 | Grotenhuis | 604/191 |
| 4,681,567 | 7/1987 | Masters et al. | 604/198 |
| 4,693,708 | 9/1987 | Wanderer et al. | 604/198 |
| 4,695,274 | 9/1987 | Fox . | |
| 4,702,738 | 10/1987 | Spencer | 604/198 |
| 4,710,170 | 12/1987 | Haber et al. | 604/110 |
| 4,723,943 | 2/1988 | Spencer | 604/198 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,772,272 | 9/1988 | McFarland | 604/198 |
| 4,816,022 | 3/1989 | Poncy | 604/198 |

Primary Examiner—John D. Yasko
Attorney, Agent, or Firm—Hill, Van Santen, Steadman & Simpson

[57] ABSTRACT

An adapter for mounting a protective sleeve or needle guard on a syringe or other needle fitting is provided including a first locking portion for engagement with a locking portion at an end of a syringe, a needle mount at an opposite side of the adapter, and engaging means for selectively engaging the protective sleeve or needle guard into at least a needle protecting position. The needle mount can be separable from the adapter, or can be integrally formed therewith.

9 Claims, 2 Drawing Sheets

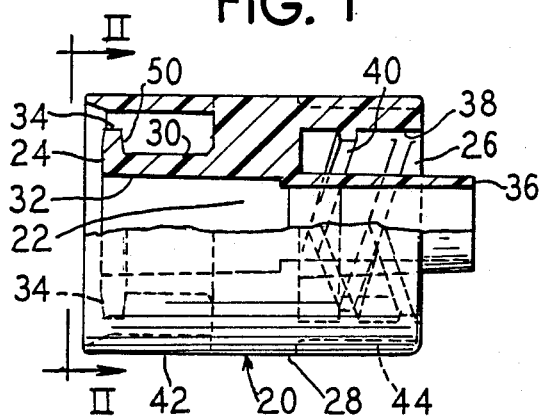
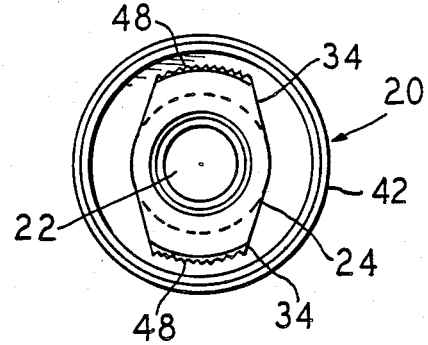
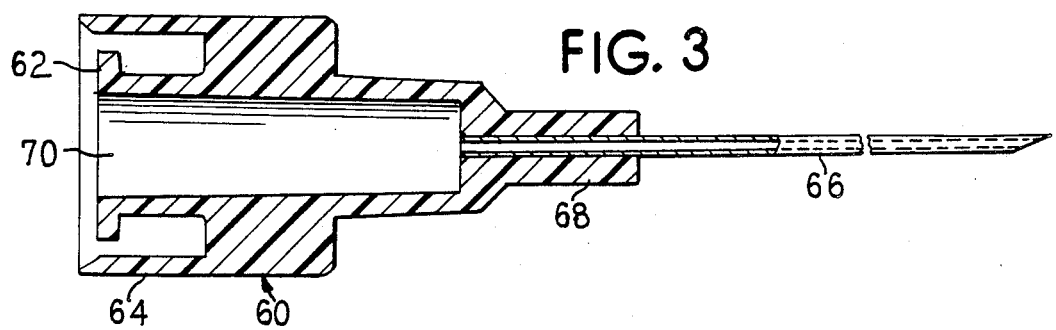
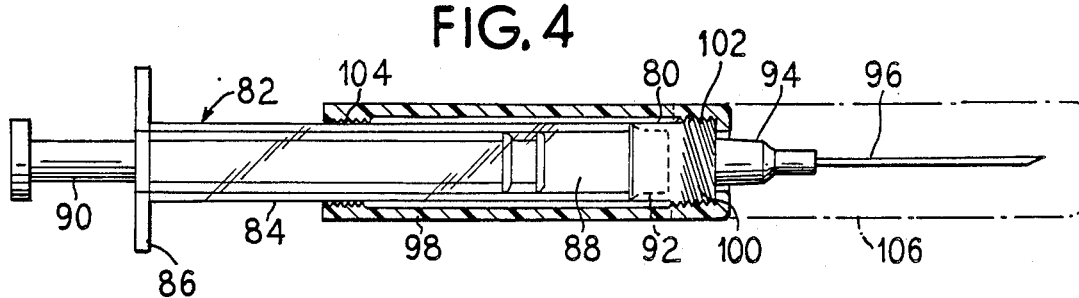
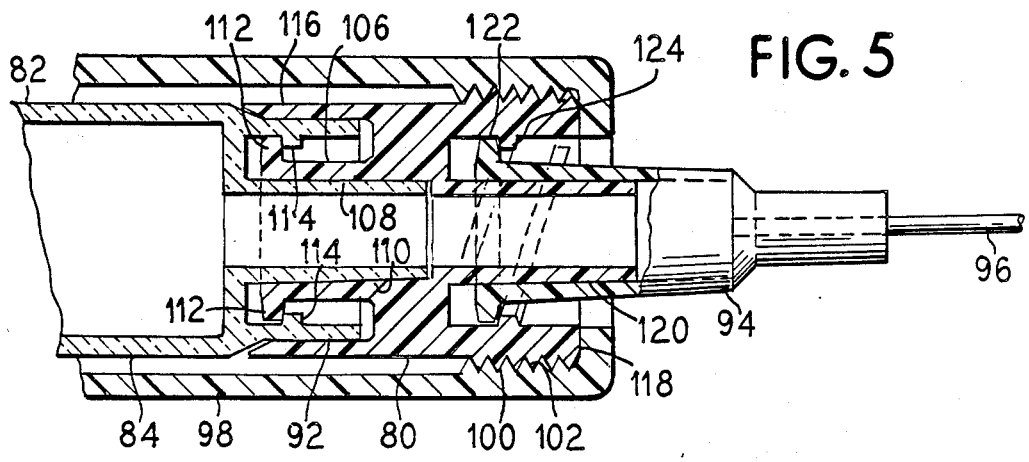

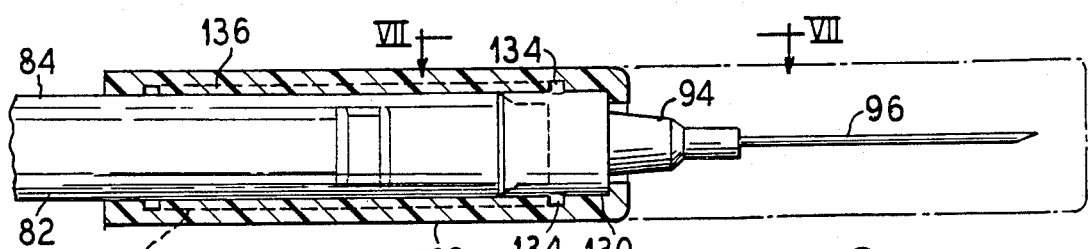
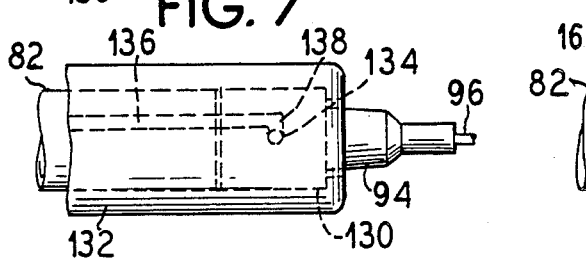
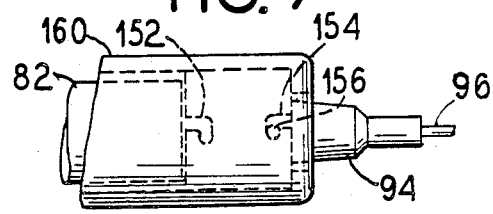
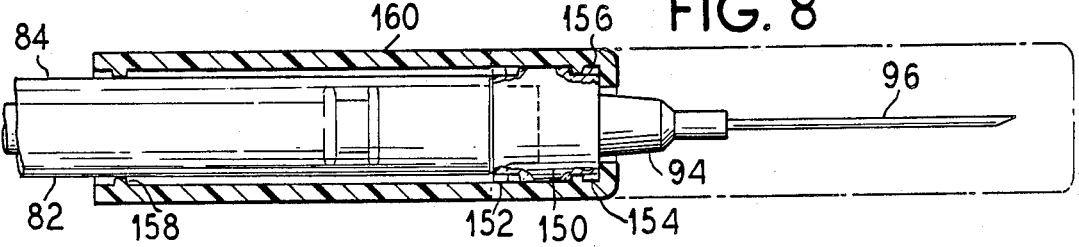
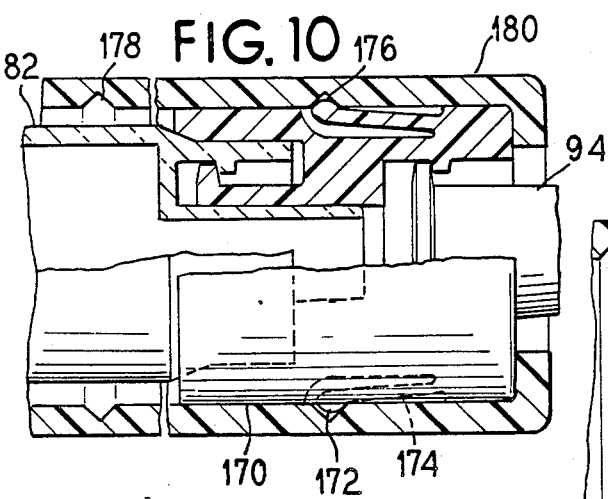
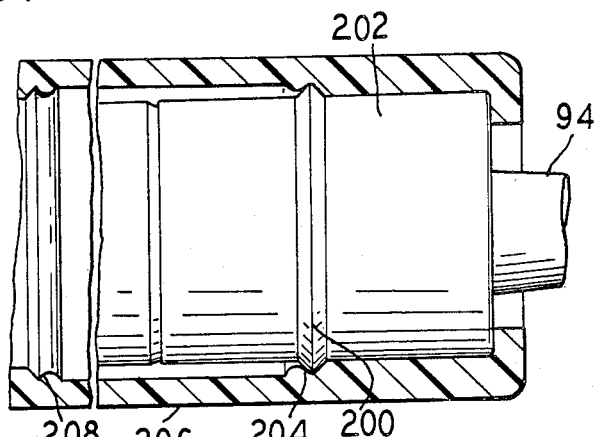
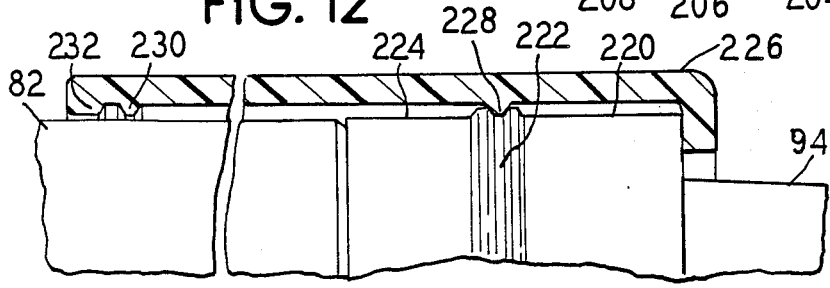

SAFETY SLEEVE ADAPTER

BACKGROUND OF THE INVENTION

1. Field of the Invention

The present invention relates generally to an adapter for selectively engaging a protective sleeve or needle shield over a hypodermic needle.

2. Description of the Related Art

The use of needles, such as hypodermic needles, by medical personnel is common place. During the use of such needles, the medical personnel occasionally unintentionally stick themselves with the needle intended for the patient. Such needle sticks most commonly occur after the needle has been used on the patient, such as for an injection, a transfusion, or the taking of blood, and an attempt is being made to recap the needle. The needle then carries bacteria or viruses from the patient and the needle stick can result in transmittal of the illness to the medical personnel treating the patient. Two factors which aggravate the problem are long hours put in by medical personnel which causes lack of attention and reduced coordination during the use of the needle, and an increase in diseases which are transmittable by a contaminated needle such as, for example, acquired immune deficiency syndrome (AIDS).

In response to the growing problem of transmittal of diseases by inadvertent needle sticks, numerous syringe safety devices have been developed, including, for instance, a syringe safety sleeve, U.S. Pat. No. 4,743,233, by one of the coinventors of the present application. In the preferred embodiments, a sleeve is provided for sliding engagement over a syringe barrel between a first position protecting the needle from contact and a second position exposing the needle for use. The sleeve is fastenable in position by threaded portions on the syringe barrel engaging cooperating threaded portions on the interior surface of the sleeve, or by a projection and channel arrangement. In each instance, a modification of the standard syringe barrel is required for securing the sleeve in the needle protecting position.

Other shielded syringe needles are also known, including a shielded hypodermic syringe as shown in U.S. Pat. No. 4,425,120 in which a needle guard is locked into position to protect the needle by a track on the internal surface of the guard and by track engaging members on the barrel. The needle guard includes a guard tube and an inner sleeve, the sleeve having a pair of tracks opening at opposite ends thereof for accepting the track engaging members.

In Spencer U.S. Pat. No. 4,723,943 is disclosed a sheath syringe in which the sheath has a longitudinal groove to engage a guide lug on the syringe body.

In the Mitchell U.S. Pat. No. 4,631,057 is disclosed a shielded needle having a needle guard which is locked in the extended position by interlocking members carried on the needle guard and by a collar mounted on the body of the syringe.

A distinct disadvantage with the known needle protecting devices is that modification of the syringe barrel with some type of engaging means to hold the needle guard or sleeve in the needle protecting position is required. This prevents the known safety devices from being used with readily available unmodified syringes including those currently in stock at health care facilities.

SUMMARY OF THE INVENTION

It is an object of the present invention to enable needle sleeves and guards to be used on unmodified syringes and needle fittings. Another object of the present invention is to permit selective use of sleeves and needle guards when desired without requiring duplication of supplies. A further object of the present invention is to permit the use of a variety of sleeves and needle guards on unmodified syringes and needle fittings.

These and other objects are achieved in an adapter for selective engagement with a protective sleeve or needle guard, the adapter being selectively mountable on a syringe or other needle fitting. As used herein, the term needle fitting generically refers to fittings, mountings and connectors for hypodermic needles, intravenous needles, transfusion needles, trocars, and the like. Since it is also possible to utilize the present invention for other sharp instruments, the term needle fitting is also deemed to cover mounts for probes, picks and other sharp objects for which protection from inadvertent injury is desired.

The present adapter includes a connector for connection to the syringe or needle fitting, a mounting such as a means for mounting a needle extending in the opposite direction from the connector, and means for selective engagement of the sleeve or needle guard with the adapter so that the sleeve or guard is fastenable in a needle protecting position. The connector is adapted for connection to a syringe or needle fitting and, as such, has the necessary structure for cooperative engagement therewith. A widely used connector structure in medical devices is a Luer lock connector. A preferred embodiment of the present invention includes one portion of a Luer lock connector for connection to syringes and needle fittings that have the cooperating other portion of the Luer lock connector. Other types of connectors for connecting the present adapter to a syringe or needle fitting are contemplated as well. The Luer lock connector portion of the present adapter can be unmodified or can also be modified, such as to provide an increase in the force required for disengagement of the connector portions.

Likewise, a Luer lock connector is a common needle mounting means so that the means for mounting a needle on the present adapter in one embodiment includes a Luer lock connector portion for engagement with a cooperating Luer lock connector formed on the needle. Other types of mounts and connectors for mounting the needle on the adapter are also within the realm of the present invention, including the straight forward approach of mounting the needle directly on the adapter without requiring an additional connector means.

The means for selectively engaging the sleeve or needle guard on the adapter can take a wide variety of forms. For instance, if a sleeve or needle guard with an internally threaded connector is used, then the adapter includes an externally threaded portion for engagement with the sleeve or guard. Similarly, if a channel and projection engagement means are provided for securing the sleeve, then the adapter includes the cooperating portion of the channel and projection engagement means. Snap fittings, flexible connectors, and other types of movement restricting and/or engaging means may also be provided between the sleeve and adapter.

Embodiments of the inventive adapter for use on syringes is preferably relative short and, therefore, does not add an appreciable length to the syringe. However, for embodiments used on transfusion needles and the like, a longer adapter body may be desirable to accommodate the sleeve as it slides between the needle protecting and needle exposing positions and still provide a grasping surface for gripping to release the engaging means.

The size of the adapter is adapted to device on which it is used and, of course, to the size of the sleeve it carries. There, however, need not be exact correspondence in size, since a larger adapter and sleeve will effectively protect a smaller syringe for example.

The present invention is versatile in that a protected needle or instrument is provided in place of an unprotected needle in every foreseeable use of hypodermic needles and other sharp instruments. It is possible with the present invention to provide a protected needle on hypodermic syringes, to provide a protected needle in place of unprotected transfusion needles and blood drawing needles The same adapter and sleeve can be used with numerous syringes and the like and can even be used with syringes of different sizes.

BRIEF DESCRIPTION OF THE DRAWINGS

FIG. 1 is a side elevational view, partially in cross section, of a first preferred embodiment of an adapter according to the principles of the present invention;

FIG. 2 is an end elevational view of the adapter of FIG. 1 including a toothed locking surface on a first connector portion for increasing engagement forces;

FIG. 3 is a longitudinal cross section of a second preferred embodiment of an adapter according to the present invention;

FIG. 4 is a side elevational view, partially in cross section, of an adapter of the present invention mounted on a syringe and including a sleeve or needle guard;

FIG. 5 is an enlarged longitudinal cross section of a portion of FIG. 4 showing the engagement of the various elements thereof;

FIG. 6 is a side elevational view partially in cross section of the adapter mounted on a syringe and including another embodiment of a sleeve engaging means;

FIG. 7 is a plan view of a portion of FIG. 6 showing the engaging means in greater detail;

FIG. 8 is a side elevational view, partially in cross section, of a further embodiment of the engaging means for the present adapter;

FIG. 9 is a plan view of a portion of FIG. 8 showing the engaging means in greater detail;

FIG. 10 is an enlarged side elevational view partially in cross section of yet another embodiment of an engaging means for selectively fastening a sleeve on the present adapter;

FIG. 11 is an enlarged cross section of yet another embodiment of an engaging means for use with the present adapter; and FIG. 12 is an enlarged partial cross section of yet a further engaging means for use with an adapter of the present invention.

DESCRIPTION OF THE PREFERRED EMBODIMENTS

Referring first to FIG. 1, a first preferred embodiment of an adapter according to the invention is shown and includes an adapter body 20 having an axially extending central channel 22, a first connector portion 24 and a second connector portion 26 opposite the first connector portion 24. A sleeve, or needle guard, engagement surface 28 is also provided on an outer cylindrical surface of the adapter body 20. More specifically, the first connector portion 24 is a male Luer lock with a cylindrical portion 30 having a slightly tapered inner surface 32. At the end of the cylindrical portion 30 are a pair of opposed ears 34 for securing the Luer lock portion 24 into a cooperating Luer lock portion, such as a female Luer lock portion on a hypodermic syringe or a needle fitting.

At an opposite end of the adapter 20 is the female Luer lock portion 26 having a central slightly tapered cylinder portion 36 and an interior threaded surface 38 having thread members 40. The Luer lock connector portions 24 and 26 of the illustrated embodiment are substantially similar to the known Luer lock connector portions found on currently available medical devices such as syringes and the like.

The outside engagement surface 28 of the adapter body 20 includes means for selective engagement with a protective sleeve or needle guard as will be discussed in greater detail hereinafter. The embodiment shown in FIG. 1 includes optional features which may be provided on the adapter. In particular, an annular flange 42 may be provided extending axially about the male connector portion 24. The flange 42 extends about the cooperating connector portion to which the connector 24 is connected and provides additional support for the adapter 20 on the syringe or needle fitting. The flange 42 may also provide a substantially continuous surface with the outer surface of the syringe barrel, for example. A second optional feature of the embodiment of FIG. 1 is a reduced exterior diameter of the wall surrounding the female connecting portion 26 in the region 44. This reduced diameter region 44 provides clearance when using the present device and also reduces the quantity of material required, particularly for larger diameter adapters. Whether these optional features are utilized depends upon many considerations including the size of the adapter, the size of the syringe or needle fitting onto which the adapter is to be connected, and the stability required of the particular sleeve or needle guard used.

In FIG. 2, an end view of the adapter 20 of FIG. 1 shows the flange 42 encircling the male connector portion 24 which includes the ears 34 of the Luer lock connector. The outside surfaces of the ears 34 include teeth 48 for increased frictional engagement between the ears 34 and a cooperating female Luer lock portion to prevent unintentional disengagement of the adapter 20 during manipulation of the sleeve engaging means or needle connector 26. It is also contemplated to utilize other friction increasing means instead, including teeth or a roughened surface on a rear surface 50 of the ears 34 (shown in FIG. 1). Alternately, the ears 34 may have a greater diameter than usual to increase the frictional fit of the male connecting portion 24 in the female connecting portion to which it is connected, or the ears 34 may be thicker to cause deformation of the female Luer lock connector portion or to provide greater contact with the threads 40. It is also contemplated to provide positive locking means, such as projections and recesses on the contacting surfaces of the connector portions.

In FIG. 3 it is shown an embodiment of the present adapter 60 which includes a male connecting portion 62 formed by a Luer lock portion as in the embodiment of FIG. 1, as well as flanges 64 encircling the male connector portion 62. Extending from the front of the adapter 60 is an alternate means for mounting a hypodermic needle 66 which includes a needle mount 68 integrally formed with the adapter 60. A central channel 70 through the adapter 60 is in fluid communication with the needle 66. The embodiment of FIG. 3 avoids the necessity of providing a separable needle mount for the adapter 60. It is possible, of course, to provide other needle mounting means, including the Luer slip connection as found on commercially available syringes.

In FIG. 4 is seen one application of an adapter 80 in use on a syringe 82 which includes a cylindrical barrel 84 having opposed finger tabs 86 and a central cavity 88 along which slides a plunger 90. At a first end of the syringe 82 is a female Luer lock fitting 92 onto which is connected the male connector portion (not shown) of the adapter 80. A needle mount 94 and hypodermic needle 96 are connected in the adapter 80 extending substantially axially of the syringe 82 and a sleeve or needle guard 98 is engaged on the adapter 80. In the illustrated embodiment, the adapter 80 includes a threaded exterior surface 100 and the sleeve or needle guard 98 has first and second threaded portions 102 and 104 for selective threaded engagement with the adapter threads 100.

FIG. 4 illustrates in solid outline the sleeve or needle guard 98 in a needle exposing, or in-use, position which is maintained by threaded engagement of the threads 100 and 102. By rotating the sleeve or needle guard 98 to release the threads 102 from the threads 100 of the adapter 80 and by subsequently sliding the sleeve 98 forward, the threads 104 on the opposite end of the sleeve 98 can be threadably engaged on the threads 100 of the adapter 80 to place the sleeve or needle guard 98 in the needle protecting position 106 illustrated in broken outline.

Of course, the number of threads on the threaded portions and the pitch of the threads is freely selectable to require fewer or greater rotations of the sleeve 98 to engage and disengage the sleeve 98 from the adapter 80. Therefore, it is within the scope of the present invention to provide a threaded connection requiring only a partial turn of the sleeve 98 on the adapter 80. It is also contemplated to provide only the second threaded connection 104 for engagement with the threaded surface 100 of the adapter 80, since it is not necessary that the sleeve 98 be securely maintained in the needle exposing position. The sleeve can be held in the needle exposing position by a simple friction fit between the adapter and sleeve, regardless of the engaging means used.

As illustrated in FIG. 5, the exterior diameter of the adapter 80 is substantiallly the same as the exterior diameter of the syringe barrel 84 and a generally continuous surface is present at the junction of the syringe barrel 84 and the adapter 80, which may be required with some forms of sleeves or needle guards to prevent catching or engaging of the sleeve engaging means in the gap between the barrel 84 and the adapter 80. However, with the threaded engagement illustrated in FIGS. 4 and 5 or with some other engaging means, this may not be necessary. For example, the diameter of the barrel 84 and the adapter 80 need not be the same, or a gap may be present at the outer surface between the barrel and the adapter. For instance, a smaller diameter syringe barrel may be connected to the illustrated adapter when required.

Also illustrated in FIG. 5 is the interconnection of the various Luer lock connectors including the male Luer lock connector portion 106 of the adapter 80 received in the female Luer lock portion 92 at the first end of the syringe 82. In particular, the tapered interior surface 108 fits snuggly against a tapered exterior surface 110 of the female Luer lock connector 92 and is held in place by the engagement between ears 112 and threads 114. Although not required in this embodiment, optional flanges 116 provide lateral stability to the adapter 80 when engaged on the first end of the syringe 82.

Like the Luer lock connection between the adapter 80 and the syringe 82, a Luer lock connector 118 on the adapter 80 for connection to the needle mount 94 has securely engaged tapered faces 120 held together by the engagement between ears 122 on the male Luer lock portion of the needle mount and threads 124 on the female Luer lock portion 118. In the illustrated embodiment, the threaded surface 100 is provided adjacent the needle end of the adapter 80 lying over the female Luer lock connector portion 118. By providing the threads 100 in this position, the length of the shield or needle guard 98 required to completely encase the needle 96 when in the needle covering position is less. It is, however, also possible that the threaded engaging means or other engaging means may be positioned at any other location along the length of the adapter 80. It is contemplated that the engaging means threads 100 be reverse threaded relative to the Luer lock threads, or that the two Luer lock connectors be reverse threaded relative to one another to prevent inadvertent release of one connection when releasing another.

FIG. 6 illustrates another embodiment of the present invention including an alternate engaging means between an adapter 130 and a sleeve or needle guard 132. The alternate engaging means includes projections or pegs 134 extending from opposite surfaces of the adapter 130 and engaging into channels 136 in the sleeve 132. The channels 136 can extend completely through the surface of the sleeve 132 or, as illustrated, can extend only partly therethrough. Instead of a pair of opposed projections 134 and similarly arranged channels 136, it is also contemplated to include only a single projection 134 and channel 136, or, alternately, to provide more than two such projections and channels providing engagement means between the adapter and the sleeve.

By reference to FIGS. 6 and 7, it can be seen that the sleeve 132 also includes rotationally extending channel portions 138 which are constricted somewhat relatively to the size of the projections 134. The rotationally extending channel portions 138 are at each end of the channels 136 in the preferred embodiment. The projections 134 are moved into the channel portions 138 to lock the sleeve 132 in each of two positions. The sleeve 132 is rotated slightly to move the projection 134 from the rotationally extending portion 138 and into the axially extending channel 136 for sliding movement of the sleeve 132 between the needle exposing position shown in solid outline and the needle covering position shown in broken outline in FIG. 6.

A further embodiment is illustrated in FIGS. 8 and 9 and includes an adapter 150 having channel portions 152 and 154 for receiving inwardly directed projections 156 and 158 at opposite ends of a sleeve or needle guard 160. By comparing FIGS. 8 and 9, it can be seen that projections 156 are engaged in channels 154 in the adapter 150 when the sleeve 160 is in the needle exposing position. By rotating the sleeve 160, the sleeve 160 is slidable along the syringe barrel 84 until the projections 158 slide into the channels 152 the sleeve 160 is then rotated until the projection 158 locks into position in the channel 152 to secure the sleeve 160 in the needle covering position as shown in FIG. 8 in broken outline.

Of course, it is also contemplated to include within the scope of the present invention channels and projections which are of different configurations sizes and numbers than those illustrated in the above described Figures. This can include increasing or decreasing the number of projections or channels, eliminating portions of the channels along the length of the sleeve or otherwise manipulating the disclosed structure to carry out generally the same function.

The above described embodiments of engaging means require at least some rotational force to engage and release the protective sleeve and the adapter. It is also possible to provide engaging means not requiring a rotational engagement and/or release force, such as shown in the embodiments which follow. Embodiments which do not require a twisting or rotational engagement and release force may be suited for needle fittings which are shorter than the protective sleeve, such as a transfusion needle fitting, and, thus, do not have a rigid grasping surface available when the sleeve is in the needle exposing position.

FIGS. 10, 11 and 12 illustrate additional embodiments of engaging means between adapters and safety sleeves including, in FIG. 10, an adapter 170 having channel engaging projections 172 mounted on the end of spring arms 174. The spring arms 174 bias the projections 172 outwardly and into one of either a first groove 176 or a second groove 178 in a sleeve or needle guard 180. In the embodiment shown in FIG. 10, the sleeve 180 is moved between the two positions by exerting an axial force on the sleeve to overcome the spring force holding the projections 172 in the channel 176. Thereafter, the projections 172 snap into place in the channels 178 to hold the sleeve 180 in the second position. An embodiment in which the channels 176 and 178 are replaced by openings extending completely through the sleeve or needle guard 180 and in which the projections 172 extend through such openings and form release buttons is also contemplated. In such embodiment, the release of the projections 172 from the openings may be accomplished by pinching or otherwise pressing the release buttons into the openings so that the sleeve may be slid between the two positions.

In FIG. 11, the spring arms 174 and projections 172 are replaced by a ring 200 extending about an adapter 202. The ring 200 locks into place in either an annular groove 204 at a first end of a sleeve 206 or an annular groove 208 at an opposite end of the sleeve 206. Whereas the spring arms 174 of the embodiment shown in FIG. 10 provide the necessary flexibility for release and engagement of the engagement means between the sleeve and adapter, in the embodiment of FIG. 11 the sleeve 206 is of a sufficiently flexible material for engagement and release of the engaging means.

Not only can an annular ring be provided on the adapter for engagement into a annular channel in the sleeve, but it is also possible to provide annular ridges on the sleeve engageable into an annular channel on the adapter, as is shown in FIG. 12, in particular, an adapter 220 has a channel 222 preceded by a reduced diameter portion 224. The sleeve or needle guard 226 of the embodiment of FIG. 12 as a first annular ring 228 at a first end of the sleeve 226 and a second annular ring 230 adjacent a second end of the sleeve 226. Axial force moves the ring 228 out of the channel 222 and permits the sleeve 226 to be slid along the barrel of the syringe 82 so that the ring 230 can be engaged into the channel 222. A second, thicker ring 232 is provided behind the ring 230 to prevent the sleeve from the sliding beyond the desired needle covering position and thereby being removed from the adapter 220.

The above described embodiments are illustrative of just a few of the numerous variations of engaging means between the present adapter and a sleeve or needle guard for protecting a health care worker or other hypodermic needle user from inadvertent contact with the needle. Although shown in each of the illustrated embodiments as having a substantially cylindrical outer surface of substantially the same diameter as the barrel of the syringe on which the adapter is used, it is also contemplated that an adapter of noncylindrical configuration can also be provided when necessary and also that adapters of differing diameters than the syringes on which they are used can be also provided. In addition to their use on syringes, the present adapter is of course easily usable on transfusion needles, blood taking needles, and trocass and, indeed, on other sharp objects such as probes, picks, scalpels, and other instruments for which inadvertent contact is undesirable.

The present adapter enables protective sleeves and needle guards to be used on currently available standard hypodermic syringes and needle fittings without modification. The adapter can be provided either alone, connected to a protective sleeve or needle guard, or attached to a hypodermic syringe as a unit. The adapter may also be provided either with an integral needle mount or with a connector for a needle mount.

Although other modifications and changes may be suggested by those skilled in the art, it is the intention of the inventors to embody within the patent warranted hereon all changes and modifications as reasonably and properly come within the scope of their contribution to the art.

We claim:

1. An adapter for selective engagement with a sleeve for protective shielding of a needle, comprising:
   an adapter body;
   a connector portion on said adapter body;
   means for removably mounting a needle on said adapter body, said means for removably mounting a needle including a female portion of a Luer lock connector for receiving a cooperating male portion of a Luer lock connector having said needle integral therewith; and
   means on said adapter body for selective engagement with said sleeve when said sleeve is in a forward position shielding said needle.

2. An adapter for selectively mounting a sleeve on a hypodermic syringe for use with a needle, the hypodermic syringe having a first portion of a first connector fitting at a first end, the adapter comprising:
   a second portion of the first connector fitting on said adapter being selectively fastenable to the first portion of the first connector fitting on the hypodermic syringe;
   means on said adapter for engaging the sleeve, said engaging means selectively firmly securing the sleeve in a first position substantially shielding the needle, said engaging means permitting the sleeve to move to a position exposing the needle for use when not firmly secured in said engaging position, said sleeve covering at least a portion of a barrel of said syringe when in a position exposing the needle for use, said engaging means being connected to said second portion of said connector so that the sleeve is secured relative to the hypodermic syringe when said engaging means selectively secures the sleeve; and a portion of a second connector extending from said adapter in a direction opposite said second portion of the first connector, said portion of said second connector being selectively engagable to a cooperating connector portion on the needle for selective fastening of the needle to said adapter.

3. An adapter as claimed in claim 2 wherein said second connector is a Luer lock connector.

4. A needle shield for use on a hypodermic syringe that has a syringe barrel and a female Luer lock portion at a first end of the syringe barrel, comprising:

a male Luer lock portion selectively engagable to the female Luer lock portion of the syringe barrel;

a hollow cylindrical body connected to said male Luer lock portion, said cylindrical body extending from the first end of the syringe barrel substantially in alignment with the syringe barrel when said male Luer lock portion is engaged with the female Luer lock portion, said cylindrical body having a diameter substantially the same as a diameter of the syringe barrel;

a hollow sleeve being slidably mounted on and lying substantially coaxial with said cylindrical body, said sleeve having a length substantially greater than a length of said cylindrical body;

means for mounting a hypodermic needle on a said cylindrical body extending substantially axially of the syringe barrel when said male Luer lock portion as engaged to the female Luer lock portion of the syringe barrel, said means for mounting a hypodermic needle includes a second female Luer lock portion on said cylindrical body opposite and substantially in axial alignment with said male Luer lock portion, said second Luer lock portion being selectively engagable to a second male Luer lock portion on a hypodermic needle; and means for selectively fastening said sleeve in at least a needle shielding position with said sleeve extending about and beyond an end of said needle, said selectively fastening means enabling said sleeve to slide to a second position exposing said needle for use when not fastened.

5. A needle shield as claimed in claim 4, wherein said means for selectively fastening said sleeve includes a first threaded portion on said cylindrical body and a second cooperating threaded portion on said sleeve.

6. A needle shield as claimed in claim 4, wherein said means for selectively fastening said sleeve includes a projection extending from said cylindrical body and means on said sleeve for selective engagement with said projection.

7. A needle shield as claimed in claim 6, wherein said means on said sleeve is a channel into which said projection extends, said channel having a constricted portion selectively engageable with said projection to fasten said sleeve in said needle shielding position.

8. A needle shield as claimed in claim 4, wherein said means for selectively fastening said sleeve includes an annular channel in said cylindrical body and an annular flange on said sleeve for engagement in said annular channel.

9. A needle shield as claimed in claim 4, wherein said means for selectively fastening said sleeve includes a projection on an inner surface of said sleeve and a catch recess on an outer surface of said cylindrical body engaging said projection when said sleeve is in said needle shielding position.

* * * * *